(12) United States Patent
Benoit et al.

(10) Patent No.: US 10,487,650 B2
(45) Date of Patent: Nov. 26, 2019

(54) FORMATION STABILIZATION WORKFLOW

(71) Applicant: HALLIBURTON ENERGY SERVICES, INC., Houston, TX (US)

(72) Inventors: Denise Nicole Benoit, Houston, TX (US); Kurt William Hoeman, Houston, TX (US); Ajish Potty, Stafford, TX (US); Venkata Satya Srikalyan Bhamidipati, Kingwood, TX (US); Jim Weaver, Duncan, OK (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 262 days.

(21) Appl. No.: 15/506,016

(22) PCT Filed: Nov. 6, 2014

(86) PCT No.: PCT/US2014/064263
§ 371 (c)(1),
(2) Date: Feb. 23, 2017

(87) PCT Pub. No.: WO2016/072989
PCT Pub. Date: May 12, 2016

(65) Prior Publication Data
US 2017/0241261 A1    Aug. 24, 2017

(51) Int. Cl.
*E21B 49/02*    (2006.01)
*C09K 8/03*     (2006.01)
*C09K 8/56*     (2006.01)
*E21B 21/06*    (2006.01)
*E21B 43/26*    (2006.01)
*G01N 11/00*    (2006.01)

(52) U.S. Cl.
CPC ............ *E21B 49/02* (2013.01); *C09K 8/03* (2013.01); *C09K 8/56* (2013.01); *C09K 2208/12* (2013.01); *E21B 21/062* (2013.01); *E21B 43/26* (2013.01); *G01N 11/00* (2013.01)

(58) Field of Classification Search
CPC ... E21B 49/00; E21B 21/062; C09K 2208/12; C09K 8/03; C09K 8/56
See application file for complete search history.

(56) References Cited

U.S. PATENT DOCUMENTS

| 6,432,717 B1 | 8/2002 | Fernando | |
| 10,302,798 B2* | 5/2019 | Benoit | ............... G01N 15/082 |
| 2009/0264595 A1 | 10/2009 | Patterson | |

(Continued)

OTHER PUBLICATIONS

International Search Report and Written Opinion for International Application No. PCT/US2014/064263 dated Aug. 4, 2015. (8 pages).

(Continued)

*Primary Examiner* — John Fitzgerald
(74) *Attorney, Agent, or Firm* — Haynes and Boone, LLP

(57) ABSTRACT

Method of selecting an optimum formation stabilization treatment for subterranean formations is described. The methods include obtaining formation material, adding a test fluid to the formation material to form a first mixture, adding the test fluid to the formation material to form a second mixture, agitating the first and second mixtures, measuring capillary suction time of the first mixture, and measuring turbidity of the second mixture.

20 Claims, 5 Drawing Sheets

(56) References Cited

U.S. PATENT DOCUMENTS

| | | |
|---|---|---|
| 2010/0307746 A1 | 12/2010 | Dakin et al. |
| 2012/0152548 A1 | 6/2012 | Hinkel et al. |
| 2015/0210913 A1* | 7/2015 | Gupta ..................... C09K 8/68 |
| | | 166/305.1 |
| 2017/0241972 A1* | 8/2017 | Bhamidipati ........ G01N 33/241 |
| 2018/0202289 A1* | 7/2018 | Benoit .................... E21B 49/02 |
| 2018/0202957 A1* | 7/2018 | Benoit ................. G01N 15/082 |

OTHER PUBLICATIONS

Weaver et al., "Stabilizing Fracture Faces in Water-Sensitive Shale Formations," Society of Petroleum Engineers, 2011, pp. 1, 7.

\* cited by examiner

FORMATION STABILIZATION WORKFLOW

CROSS-REFERENCE TO RELATED APPLICATION

The present application is a U.S. National Stage patent application of International Patent Application No. PCT/US2014/064263, filed on Nov. 6, 2014, the benefit of which is claimed and the disclosure of which is incorporated herein by reference in its entirety.

BACKGROUND

The present invention relates generally to methods of selecting an optimum formation stabilization treatment for a subterranean formation.

It is well known that the production of oil and gas is many times hindered by formation damage. Most damage occurs due to introduction of fluids and high pump rates that cause swelling and/or migrating in the formation. Formations are prone to water-sensitivity, which can cause damage through swelling, softening, dissolving, forming precipitates, sloughing and/or generating migrating fines. All of these can decrease production or induce wellbore damage.

In some formations, clays or fines may already be present or fines may be generated during formation treating activity. In some instances, the formation is stable causing no obstruction to the flow of hydrocarbons through the subterranean formation. However, when the formation is not stable, the minerals can swell and/or fines can migrate through the formation until they become lodged in pore throats, thereby decreasing the permeability of the formation.

Recommendations for formation stabilization treatments typically rely on expensive instrumentation, time-consuming methods, and hard to obtain core materials; which are not feasible to run on a well-to well basis at a field lab locale. Thus, there is a need for improved methods that enable the selection of an optimum treatment for subterranean formations.

BRIEF DESCRIPTION OF THE DRAWINGS

The following figures are included to illustrate certain aspects of the present invention, and should not be viewed as an exclusive embodiment. The subject matter disclosed is capable of considerable modification, alteration, and equivalents in form and function, as will occur to those skilled in the art and having the benefit of this disclosure.

DETAILED DESCRIPTION

Figure 1:
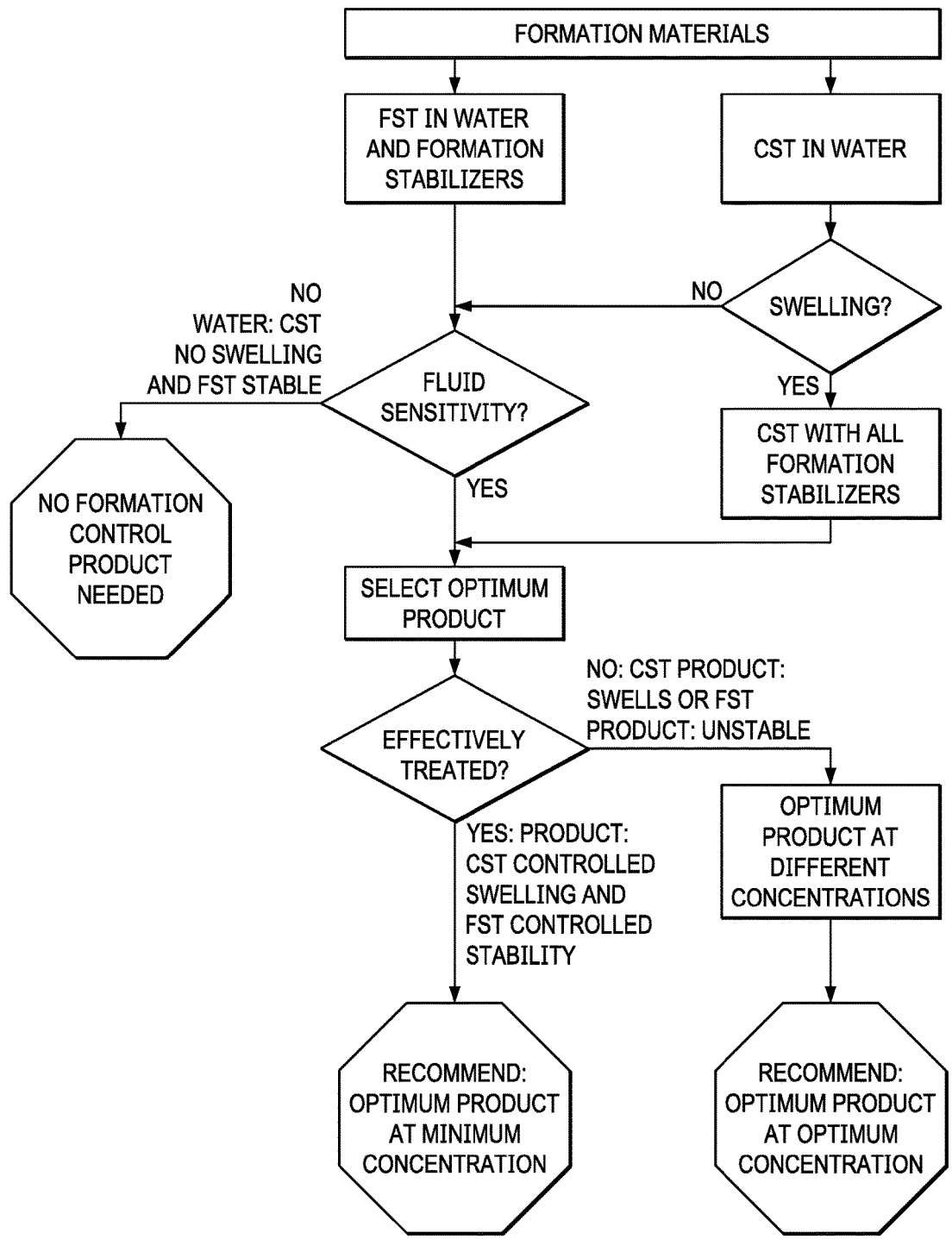
FIG. 1 shows a workflow diagram illustrating the steps involved in the selection of an optimum formation treatment product and recommended concentrations of the product according to embodiments of the present invention.

According to several exemplary embodiments, methods are provided for selecting an optimum solution based formation stabilization treatment for a subterranean formation by measuring swelling and formation stability. The methods assess formation samples for stability with proposed stimulation fluids. Formation compatibility with stimulation fluids is imperative to ensure maximum longevity and production efficiency of a well.

The methods include a workflow that provides quick, low-cost, field-lab deployable tests designed to evaluate water sensitivity of formation materials on a well-to-well basis to select an optimum formation stabilization treatment to increase oil and gas production. Through the tests, users are able to evaluate formation materials to determine water-sensitivity, looking at possible damage mechanisms including (but not limited to) swelling, fines migration, precipitate migration, formation dissolution, and formation softening. Users are also able to recommend an optimal well-specific treatment including the appropriate product and concentration.

Advantageously, the analytical workflow allows field lab personnel to use performance based assessments of easy to obtain formation materials with a range of possible treatments to rank their performance and allow for customization of treatment fluids, including (but not limited to) hydraulic fracturing fluids and drilling fluids, based on the chemistry of the particular well. The methods allow lab personnel to demonstrate the water-sensitivity of formations and rank possible treatment options.

According to several exemplary embodiments, the methods test formation materials, such as (but not limited to) drill cuttings, core sample materials, and/or even simulated formation materials.

According to several exemplary embodiments, methods of selecting an optimum formation stabilization treatment for a subterranean formation include obtaining a formation material, adding a test fluid to the formation material to form a first mixture, adding the test fluid to the formation material to form a second mixture, agitating the first and second mixtures, measuring capillary suction time of the first mixture, and measuring turbidity of the second mixture.

The Capillary Suction Time (CST) test measures the swelling tendency of formation materials in the presence of a treatment fluid. A slurry of formation materials and treatment fluid is generated, and the time required for the free liquid to travel a calibrated distance in a standard porous paper is measured. The measurement is made by placing a certain volume of slurry into a sample cylinder that is resting on a standard porous paper. Electrodes located at two different distances from the edge of the cylinder are connected with a timer. The timer starts when liquid reaches the closest electrode and then stops when it reaches the outer electrode. The time interval measured is sensitive to the amount of free water in the slurry and the permeability of the filter cake deposited. As the formation material swells, it takes up free water from the slurry, which decreases available water to wick through the filter paper. Therefore, the lower the capillary suction time, the less the formation materials swell in that treatment fluid.

Formation stability may be measured by a Formation Stability Turbidity (FST) test, which measures damage to the formation materials caused by a fluid, including but not limited to softening, fines migration and sloughing. In a short period of time, the propensity of the sample to disintegrate and release suspended fine materials is determined by measuring the turbidity of the solution. The more fines in suspension indicate that the fluid wetting and mechanical agitation process result in an increase in the rate of formation destabilization. The turbidity, in several embodiments, is monitored as a function of time and treatment. In the end, the treatment that generates the lowest turbidity is indicative of the optimum formation stabilization treatment.

According to several exemplary embodiments, the method includes three steps. The first step evaluates the formation material's sensitivity to water by monitoring the prevalence of: (a) swelling using the CST test and (b) formation stability using the FST test. These initial tests determine the amount of fluid damage that is possible for a given formation and determines the next set of steps. According to several exemplary embodiments, standard water analysis and formation X-ray diffraction analysis are also performed.

If the formation shows sensitivity to water (e.g., the results of the CST test and FST test exceed a predetermined threshold), the method moves to the second step, which evaluates and ranks possible formation stabilization treatment products for a given formation. The top performing product is determined based on percent improvement of CST and FST with the product.

The third step takes the top performing formation stabilization product, looks at the effect of product concentration on formation stabilization, and optimizes the recommended treatment for performance and fluid compatibility. Fluid compatibility studies are performed to ensure that each component in the fluid retains its intended property or function in the presence of the recommended treatment. Fluid compatibility testing can be performed through visual observation and/or viscosity testing. The final outcome is a customized product and concentration recommendation for an individual well.

Among the damaging minerals that may be present originally in the formation, or may have been introduced therein, are clay materials of the smectite (montmorillonite) group such as montmorillonite, saponite, nontronite, hectorite, beidellite, and sauconite; the kaolin group such as kaolinite, nacrite, dickite, endellite and halloysite; the illite (hydrous-mica) group such as hydrobiotite, glauconite, and illite; the chlorite group (both 7 and 14 angstrom basal spacings) such as chlorite, greenalite and chamosite; clay minerals not belonging to the above groups such as vermiculite, palygorskite (attapulgite) and sepiolite; and mixed-layer (both regular and irregular) varieties of the above minerals. The clay content of the formations can include a single species of a clay mineral or several species, including the mixed-layer types of clay. The clay-containing formations need not be composed entirely of clay, but may contain other mineral components associated therewith. The clays in the formation may be of varying shapes, such as minute, plate-like, tube-like and/or fiber-like particles having an extremely large surface area.

Formation damaging minerals do not have to be clays, but could include any minerals present that will become destabilized due to interaction with the fluids or high pump rates. For example, carbonate minerals in a formation can dissolve when an acidic fluid is introduced into the formation. According to several exemplary embodiments, the subterranean formations include fine-grained, elastic sedimentary rocks composed of different mixtures of clay minerals and other minerals such as quartz, calcite, pyrite, chlorite, feldspar, opal, cristobalite, biotite, clinoptilite, gypsum, and the like. The types of minerals and their morphology in the formation may be of varying shapes and ratios.

According to several exemplary embodiments, the formation stabilization product is any suitable chemical additive that prevents damage to formation materials in reaction to a water-based fluid and/or non-aqueous based fluids, such as oil, mineral oil, diesel, and condensate. Examples of formation stabilization products that may be used include, but are not limited to, potassium chloride, sodium chloride, ammonium chloride, tetramethyl ammonium chloride, cationic polymers, cationic surfactants, hydrophobic resins, transition metals, furfuryl alcohols, ethylene glycol, quaternary amines, bisquaternary amines and the like.

According to several exemplary embodiments, the formation stabilization product is incorporated into treatment fluid, such as a fracturing fluid or a pre-pad fluid. Hydraulic fracturing has been utilized for many years to stimulate the production of oil, gas and other formation fluids from subterranean formations. In hydraulic fracturing, a suitable fluid is introduced into a subterranean formation by way of a wellbore under conditions of flow rate and pressure, which are at least sufficient to create or extend a fracture into a desired portion of the formation. Fracturing fluid that bleeds into the fracture face often interacts with formation materials and damages permeability of the formation adjacent to the fracture. According to several exemplary embodiments, this damage can be minimized by incorporating the formation stabilization product discussed above into the fracturing fluid at an optimized concentration.

The following examples are illustrative of the compositions and methods discussed above and are not intended to be limiting.

Example 1

FIG. 1 illustrates the steps involved in determining the optimum formation stabilization product and recommended concentration.

Drill Cuttings Preparation

To reduce testing variability, drill cuttings were cleaned. A jar was filled with some drill cuttings.

A. Oil-Based Cuttings

Kerosene was poured into the jar. The jar was then gently swirled, and the kerosene was poured out into a waste container. A second kerosene rinse was then administered. After kerosene, the drill cuttings were rinsed with hexane, toluene, and methanol. The cuttings were subsequently spread out and coated with methanol to facilitate drying. The dried cuttings were then ground using a mortar and pestle and then sieved.

B. Water-Based Cuttings

A potassium chloride (KCl) aqueous solution was poured into the jar. The jar was gently swirled, and the KCl solution was poured into a waste container. A second KCl rinse was administered. After the KCl solution, the drill cuttings were rinsed with methanol. The cuttings were subsequently spread out and coated with methanol to facilitate drying. The dried cuttings were then ground using a mortar and pestle and then sieved.

Capillary Suction Time (CST) Test

A 4 mL sample of test fluid was injected into a cylinder of a CST instrument to obtain fluid blank time, and the fluid blank time was recorded. A slurry was then prepared by adding 50 mL of test fluid to a blender jar and adjusting the blender speed to generate a vortex in the fluid without overflow of the fluid. 2.00 grams of a sub-120 mesh ground drill cuttings sample was added to the blender jar and blended for 5 minutes. The blender was stopped, and the slurry was mixed again for a few seconds. 4 mL of the slurry from the blender was quickly collected from the blender and transferred into the cylinder. The slurry time was recorded. The CST value was then calculated using the equation:

$$CST\ value\ (sec) = Slurry\ time - fluid\ blank\ time$$

CST Test in Deionized Water and Formation Stabilizer Solutions

Referring to FIG. 1, CST testing was performed using deionized and source water as the test fluid. If the CST value was greater than 20 seconds in either fluid (e.g., the formation materials exhibit swelling), then additional testing was performed using 0.1 gal/1,000 gal solutions of formation stabilization products such as Cla-Web™ clay stabilization additive, Cla-Sta® XP clay stabilization additive, Cla-Sta® FS compound, and Clayfix 3™ clay-control material, which are commercially available from Halliburton Energy Services, Inc.; however any formation stabilization product from any vendor can be evaluated using the same testing procedures. The 20 second time is a calibration point that should be determined with each new set of filter papers.

If the CST value for water and source water was less than 20 seconds (e.g., the formation materials do not exhibit swelling), the optimum product was determined from the FST test. If the formation materials did not swell and did not show sensitivity to fluid, no further testing was performed because no formation control product was needed.

If the optimum product (e.g., the formation stabilization product with the lowest CST and FST value) at 0.1 gal/1,000 gal had a CST value less than 20 seconds, only a minimum concentration was needed to control formation swelling and the optimum concentration was determined from FST testing or a minimum concentration (e.g., 0.25 gal/1000 gal) was recommended. If the CST value for the optimum product (e.g., the formation stabilization product with the lowest CST and FST value) was greater than 20 seconds, the product was run at additional concentrations of 0.5, 1, 5, and 10 gal/1,000 gal.

Formation Stability Turbidity(FST) Test

For each fluid sample, 0.25 grams of −30 and +40 mesh sieved cuttings were added to 15 mL of a test fluid in a turbidity measurement glass vial, and the vial sealed. Turbidity was measured using a turbidity meter, and the turbidity value was recorded. The vials were placed on a lab rotator so that the vials were rotated end-over-end. The vials were rotated at 15 rpm for 10 minutes. Rotation was stopped, and turbidity was measured a second time for each sample vial. The vials were placed again in the lab rotator and rotated for an additional 110 minutes at 15 rpm. Rotation was stopped, and turbidity was measured a third time for each sample vial. Turbidity was then plotted over time.

FST Test in Deionized Water and Clay Stabilizer Solutions

Referring to FIG. 1, the FST test was performed using deionized water, 7% KCl, and various formation stabilization products. If the 120 minute deionized water turbidity value was greater than 200 nephelometric turbidity units (NTU) (e.g., the formation materials exhibited fluid sensitivity), the optimum product (i.e., the product that gave the best percent improvement for CST and FST) was run at different concentrations. If the 120 minute deionized water turbidity value was less than 200 NTU, no additional concentrations were run because no stabilization treatment was required.

Interpretation of Results

The data from the CST test and FST test were combined and analyzed to determine the best overall product to inhibit both swelling and fines migration.

A. Most Effective Product

For formations that exhibited both swelling and destabilization in fluids (i.e., those with a CST value greater than 20 seconds), the percent improvement for FST versus CST for each product was plotted. Percent improvement was calculated using the equation:

$$\%\ Improvement = (Water\ Value - Product\ Value)/(Water\ Value)*100$$

The product that achieved the highest percent improvement on both tests was used to determine the optimum concentration.

Figure 2:
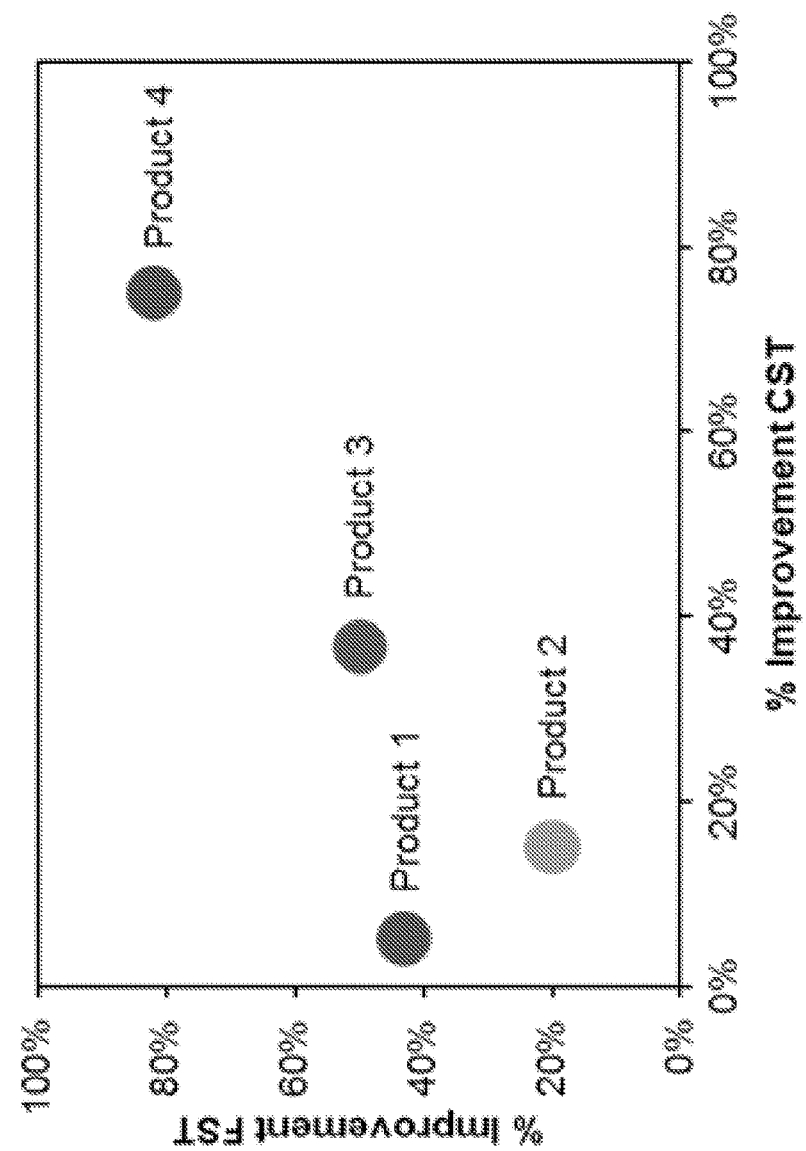
FIG. 2 shows a graph of percent improvement in formation stability against percent improvement in swelling reduction for four products according to embodiments of the present invention.

FIG. 2 illustrates a graph that compares four products by plotting the percent improvement of FST against percent improvement in CST. Based on the graph, Product 4 is the optimum product.

B. Best Concentration of Most Effective Product

If the CST value for the formation in water was less than 20 seconds and the turbidity measurement for the formation in water was less than 200 NTU, no treatment was required. If the CST value for the formation in water was greater than 20 seconds, and the CST value for the formation in all formation stabilization products was less than 20 seconds, a percent improvement of FST for the most effective product versus concentration graph was plotted to determine the optimum concentration.

If the CST value for the formation in the formation stabilization products was greater than 20 seconds, the percent improvement for each product was calculated. The highest percent improvement product was then tested at multiple concentrations to select the optimal treatment concentration. The Improvement Factor was calculated using the equation:

$$Improvement\ Factor = (\%\ Improvement\ FST + \%\ Improvement\ CST)/2$$

Figure 3:
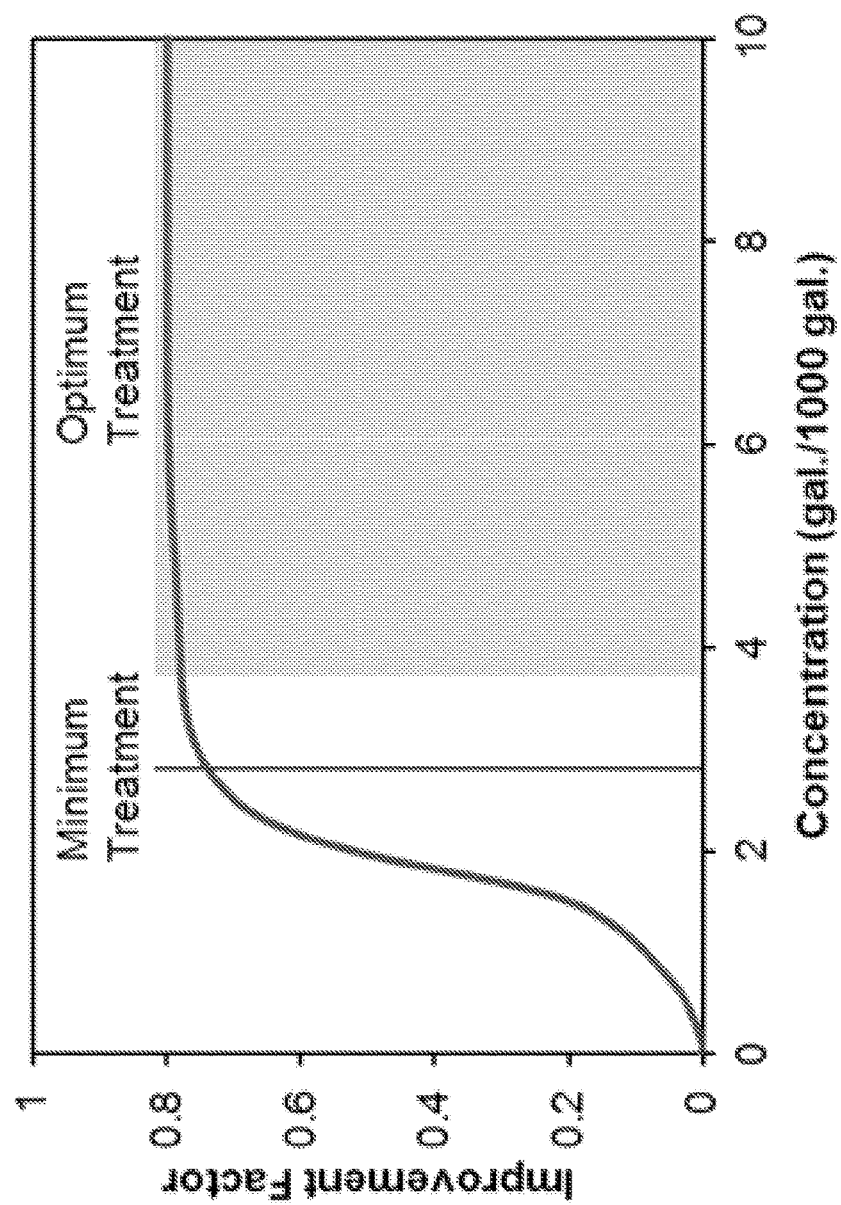
FIG. 3 shows a graph of the improvement factor against concentration according to embodiments of the present invention.

The Improvement Factor was then plotted versus concentration to determine the optimum concentration. FIG. 3 illustrates a sample graph. The optimum concentration should not be below the plateau of the graph because that is the minimum concentration necessary for protection. The graph in FIG. 3 shows that the minimum treatment concentration point is around 3 gal/1000 gal, and the recommended concentration is at 4 gal/1000 gal.

Example 2

Formation materials for five (5) different formations were tested to determine an optimum formation stabilization treatment, and the results are shown in Table 1 below. Products 1-4 are various clay stabilization or formation stabilization products.

TABLE 1

|  | Major Formation Material | Deionized Water CST (sec) | Deionized Water FST (NTU) | Improvement Factor | Treatment Winner | Treatment Concentration |
| --- | --- | --- | --- | --- | --- | --- |
| Formation 1 | Carbonate | 18 | 281 | 62 | Product 1 | 0.25 gpt |
| Formation 2 | Clay | 133 | 1000 | 49 | Product 2 | 0.5 gpt |

TABLE 1-continued

| | Major Formation Material | Deionized Water CST (sec) | Deionized Water FST (NTU) | Improvement Factor | Treatment Winner | Treatment Concentration |
|---|---|---|---|---|---|---|
| Formation 3 | Quartz | 17 | 553 | 51 | Product 3 | 0.25 gpt |
| Formation 4 | Quartz | 3 | 894 | 71 | Product 2 | 0.25 gpt |
| Formation 5 | Clay | 28 | 282 | 64 | Product 4 | 0.5 gpt |

To illustrate how the treatment winner and treatment concentration were chosen, additional details of the testing associated with Formation 2 is provided below.

CST Test and FST Test in Deionized Water and Formation Stabilization Solutions for Formation 2

The CST and FST results for Products 1-4 are provided below in Tables 2 and 3.

TABLE 2

| | CST (sec) | % Improvement |
|---|---|---|
| Deionized Water | 133 | — |
| Product 1 | 131 | 1% |
| Product 2 | 23 | 83% |
| Product 3 | 126 | 5% |
| Product 4 | 121 | 9% |

TABLE 3

| | FST (NTU) | % Improvement |
|---|---|---|
| Deionized Water | 1000 | — |
| Product 1 | 1000 | 0% |
| Product 2 | 844 | 16% |
| Product 3 | 896 | 10% |
| Product 4 | 1000 | 0% |

Figure 4:
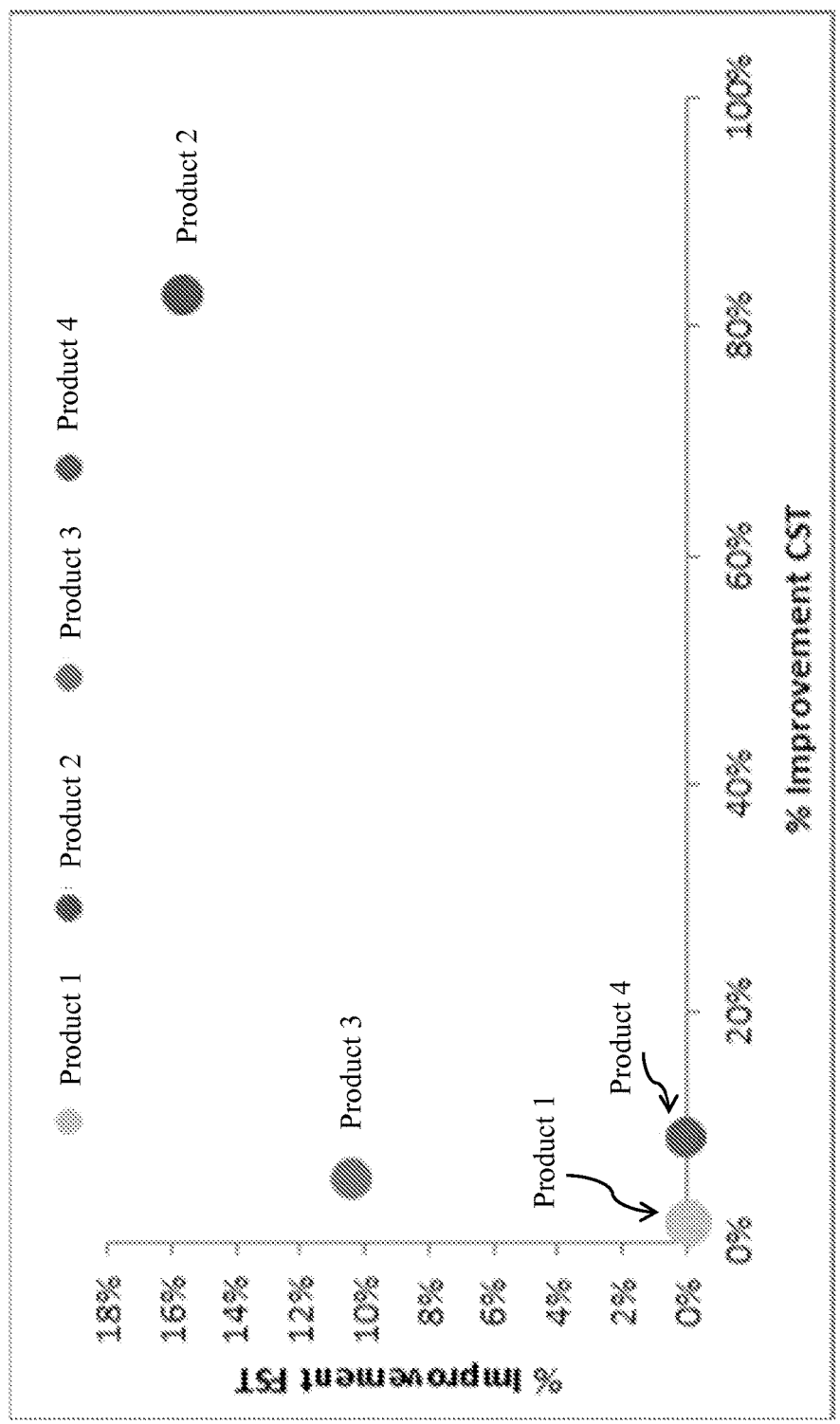
FIG. 4 shows another graph of percent improvement in formation stability against percent improvement in swelling reduction for four products according to embodiments of the present invention.

FIG. 4 illustrates a graph that compares the four products by plotting the percent improvement of FST against percent improvement in CST. Based on the graph, Product 2 is the optimum product.

The data from the CST and FST tests were combined, and an Improvement Factor for each product was calculated. The results are provided below in Table 4, and confirm that Product 2 is the best product for Formation 2.

TABLE 4

| | Improvement Factor |
|---|---|
| Product 1 | 1 |
| Product 2 | 49 |
| Product 3 | 8 |
| Product 4 | 5 |

Optimizing Concentration of Product 2

Various concentrations of Product 2 were then tested and the Improvement Factor was determined for each concentration. The concentrations and Improvement Factors are shown in Table 5 below.

TABLE 5

| | 0 gpt | 0.25 gpt | 0.5 gpt | 1 gpt | 5 gpt | 10 gpt |
|---|---|---|---|---|---|---|
| CST (sec) | 133 | 23 | 20.3 | 17.6 | 17 | 17 |
| FST (NTU) | 1000 | 656 | 491 | 454 | 531 | 492 |
| Improvement Factor | 0 | 59 | 68 | 71 | 67 | 69 |

Figure 5:
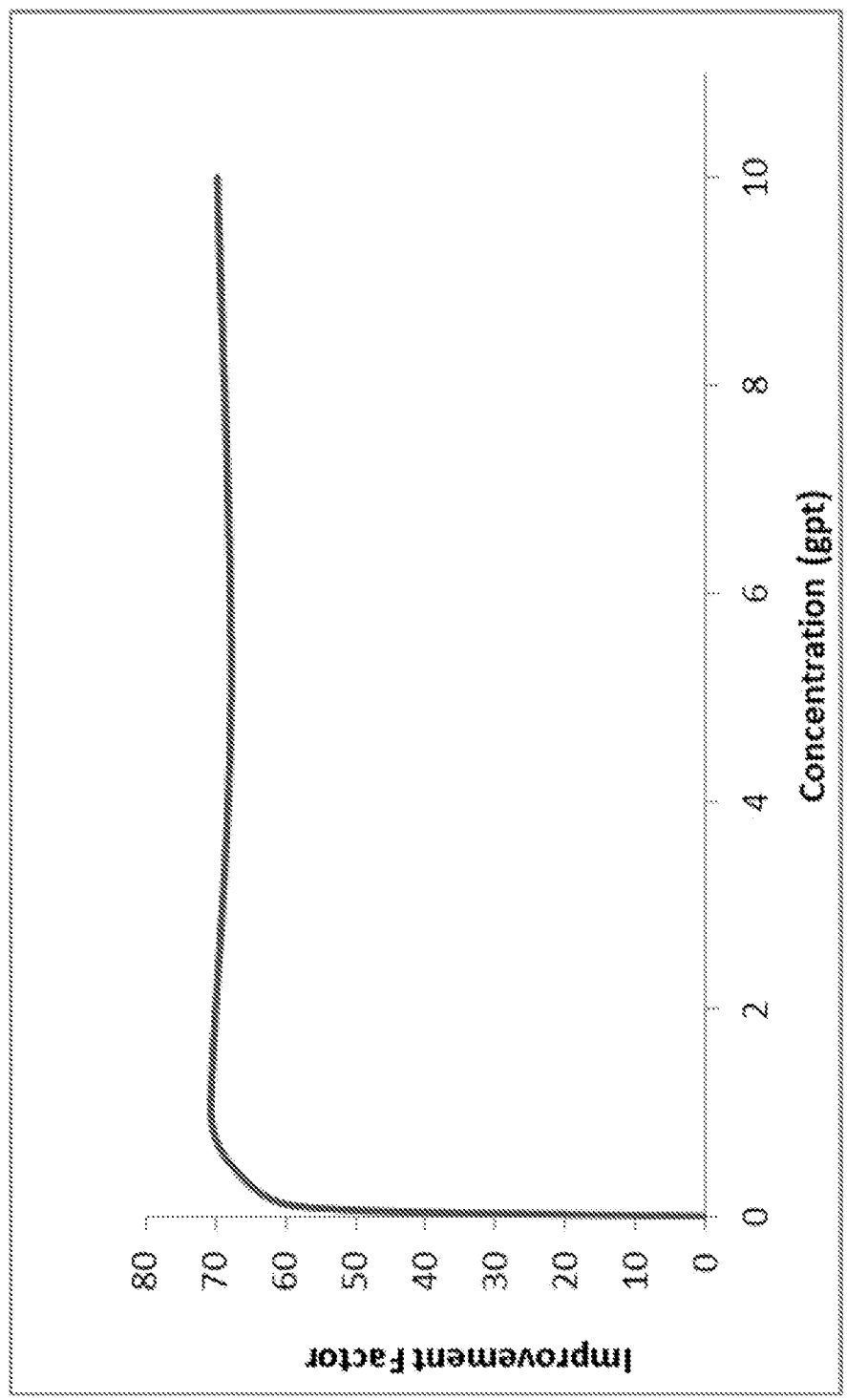
FIG. 5 shows a graph of the improvement factor against concentration according to embodiments of the present invention.

The Improvement Factor for each concentration was then plotted versus concentration to determine the optimum concentration of Product 2. FIG. 5 illustrates the graph. Based on the data and graph, the optimum concentration of Product 2 is about 0.5 gpt because the major improvement occurs by 0.25 gpt and 0.5 gpt is within the plateau of improvement and does not substantially increase after this point as concentration increases.

Although only a few exemplary embodiments have been described in detail above, those of ordinary skill in the art will readily appreciate that many other modifications are possible in the exemplary embodiments without materially departing from the novel teachings and advantages of the present invention. Accordingly, all such modifications are intended to be included within the scope of the present invention as defined in the following claims.

What is claimed is:

1. A method comprising:
   obtaining formation material;
   adding a test fluid to the formation material to form a first mixture;
   adding the test fluid to the formation material to form a second mixture;
   agitating the first and second mixtures;
   measuring capillary suction time of the first mixture; and
   measuring turbidity of the second mixture.

2. The method of claim 1, wherein the test fluid comprises water or a formation stabilizer solution.

3. The method of claim 1, further comprising determining whether the capillary suction time exceeds a predetermined value.

4. The method of claim 3, further comprising, when the capillary suction time exceeds the predetermined value, forming a plurality of additional mixtures of formation material in a plurality of test fluids and measuring the capillary suction time of the plurality of additional mixtures.

5. The method of claim 4, further comprising determining whether the capillary suction time exceeds the predetermined value for each of the plurality of additional mixtures.

6. The method of claim 5, further comprising, when the capillary suction time of each of the plurality of additional mixtures exceeds the predetermined value, measuring the capillary suction time of the test fluid that exhibited the lowest capillary suction time at different concentrations.

7. The method of claim 1, further comprising determining whether the turbidity exceeds a predetermined value.

8. The method of claim 7, further comprising, when the turbidity exceeds the predetermined value, forming a plurality of additional mixtures of formation material in a plurality of test fluids and measuring the turbidity of the plurality of additional mixtures.

9. The method of claim 8, further comprising selecting one or more of the plurality of test fluids with the lowest turbidity.

10. The method of claim 9, further comprising measuring the turbidity of the selected one or more test fluids at different concentrations.

11. The method of claim 1, further comprising:
forming a plurality of additional mixtures of formation material in a plurality of formation stabilizer solutions;
measuring capillary suction times of each of the plurality of additional mixtures; and
measuring turbidity of each of the plurality of additional mixtures.

12. The method of claim 11, further comprising determining an optimum formation stabilizer solution based on percent improvement of capillary suction time and turbidity for each formation stabilizer solution.

13. The method of claim 12, further comprising measuring capillary suction time and turbidity for the optimum formation stabilizer solution at different concentrations.

14. The method of claim 13, further comprising determining an optimum concentration of the optimum formation stabilizer solution.

15. A method comprising:
measuring capillary suction time and turbidity of formation material in water;
measuring capillary suction time and turbidity of the formation material in different formation stabilizer solutions;
calculating percent improvement of capillary suction time and turbidity for each of the different formation stabilizer solutions over water;
selecting one or more formation stabilizer solutions based on the calculated percent improvements; and
optimizing concentrations of the selected one or more formation stabilizer solutions.

16. The method of claim 15, further comprising plotting percent improvement in turbidity versus percent improvement in capillary suction time.

17. The method of claim 15, further comprising calculating an improvement factor for each of the selected one or more formation stabilizer solutions at different concentrations.

18. The method of claim 17, further comprising plotting the improvement factor for each of the selected one or more formation stabilizer solutions versus concentration.

19. A method comprising:
measuring capillary suction time and turbidity of formation material in water;
measuring capillary suction time and turbidity of the formation material in different formation stabilizer solutions;
calculating percent improvement of capillary suction time and turbidity for each of the different formation stabilizer solutions over water;
plotting percent improvement in turbidity versus percent improvement in capillary suction time on a graph;
selecting an optimum formation stabilizer solution based on the graph; and
determining an optimum concentration of the optimum formation stabilizer solution based on a graph of an improvement factor for the optimum formation stabilizer solution at different concentrations.

20. The method of claim 19, further comprising treating the formation with the optimum formation stabilizer solution at the optimum concentration.

* * * * *